United States Patent [19]

Yoon

[11] Patent Number: 5,472,429
[45] Date of Patent: Dec. 5, 1995

[54] SURGICAL INSTRUMENT STABILIZER

[76] Inventor: InBae Yoon, 2101 Highland Ridge Dr., Phoenix, Md. 21131

[21] Appl. No.: 392,655

[22] Filed: Feb. 23, 1995

Related U.S. Application Data

[62] Division of Ser. No. 170,620, Dec. 20, 1993, which is a continuation of Ser. No. 788,143, Nov. 6, 1991, abandoned.

[51] Int. Cl.⁶ .................................................. A61M 5/32
[52] U.S. Cl. ............................................ 604/178; 606/198
[58] Field of Search .................................... 606/191, 192, 606/198; 604/96, 174, 177, 178, 179, 180; 128/DIG. 26

[56] References Cited

U.S. PATENT DOCUMENTS

| | | |
|---|---|---|
| 3,039,468 | 6/1962 | Price . |
| 3,253,594 | 5/1966 | Matthews et al. . |
| 3,459,175 | 8/1969 | Miller . |
| 3,952,742 | 4/1976 | Taylor . |
| 4,077,412 | 3/1978 | Moossun . |
| 4,083,369 | 4/1978 | Sinnreich . |
| 4,555,242 | 11/1985 | Saudagar . |
| 4,608,965 | 9/1986 | Anspuch, Jr. et al. ........................ 128/4 |
| 4,666,435 | 5/1987 | Parks . |
| 4,670,008 | 6/1987 | Von Albertini . |
| 4,748,982 | 6/1988 | Horzewski et al. . |
| 4,944,732 | 9/1990 | Russo . |
| 5,002,557 | 3/1991 | Hasson . |
| 5,009,643 | 4/1991 | Reich et al. . |
| 5,073,169 | 12/1991 | Raiken . |
| 5,112,321 | 5/1992 | Hiltebrandt . |
| 5,112,347 | 5/1992 | Taberi ................................. 604/96 X |
| 5,122,122 | 6/1992 | Allgood . |
| 5,137,520 | 8/1992 | Maxson et al. . |
| 5,147,316 | 9/1992 | Castillenti . |
| 5,176,648 | 1/1993 | Holmes et al. . |
| 5,176,697 | 1/1993 | Hasson et al. . |

FOREIGN PATENT DOCUMENTS

| | | | |
|---|---|---|---|
| 0432363 | 6/1991 | European Pat. Off. . | |
| 2653424 | 6/1978 | Germany .............................. | 604/96 |
| 1113896 | 5/1968 | United Kingdom . | |

Primary Examiner—Mary Beth O. Jones

[57] ABSTRACT

A stabilizer for stabilizing a surgical instrument extending through tissue of an anatomical cavity wall includes an expandable outer member disposed on the surgical instrument and an inner member disposed between the outer member and the surgical instrument for moving the outer member between a contracted position allowing insertion of the outer member in the cavity wall and an expanded position resisting withdrawal of the outer member and the surgical instrument from the cavity wall. The outer member includes a plurality of legs, and protrusions on the inner member expand the legs outwardly from the surgical instrument in the expanded position in response to movement of the inner member. Annular, tapered ribs on the legs bite into the tissue along the thickness of the cavity wall in the expanded position to lock the surgical instrument in place in the cavity wall. The legs apply force to the protrusions in the expanded position causing the inner member to grip the surgical instrument for further stabilization. A membrane can be disposed over the outer member and a portion of the surgical instrument within the cavity to prevent trapping or jamming of tissue in the stabilizer.

29 Claims, 1 Drawing Sheet

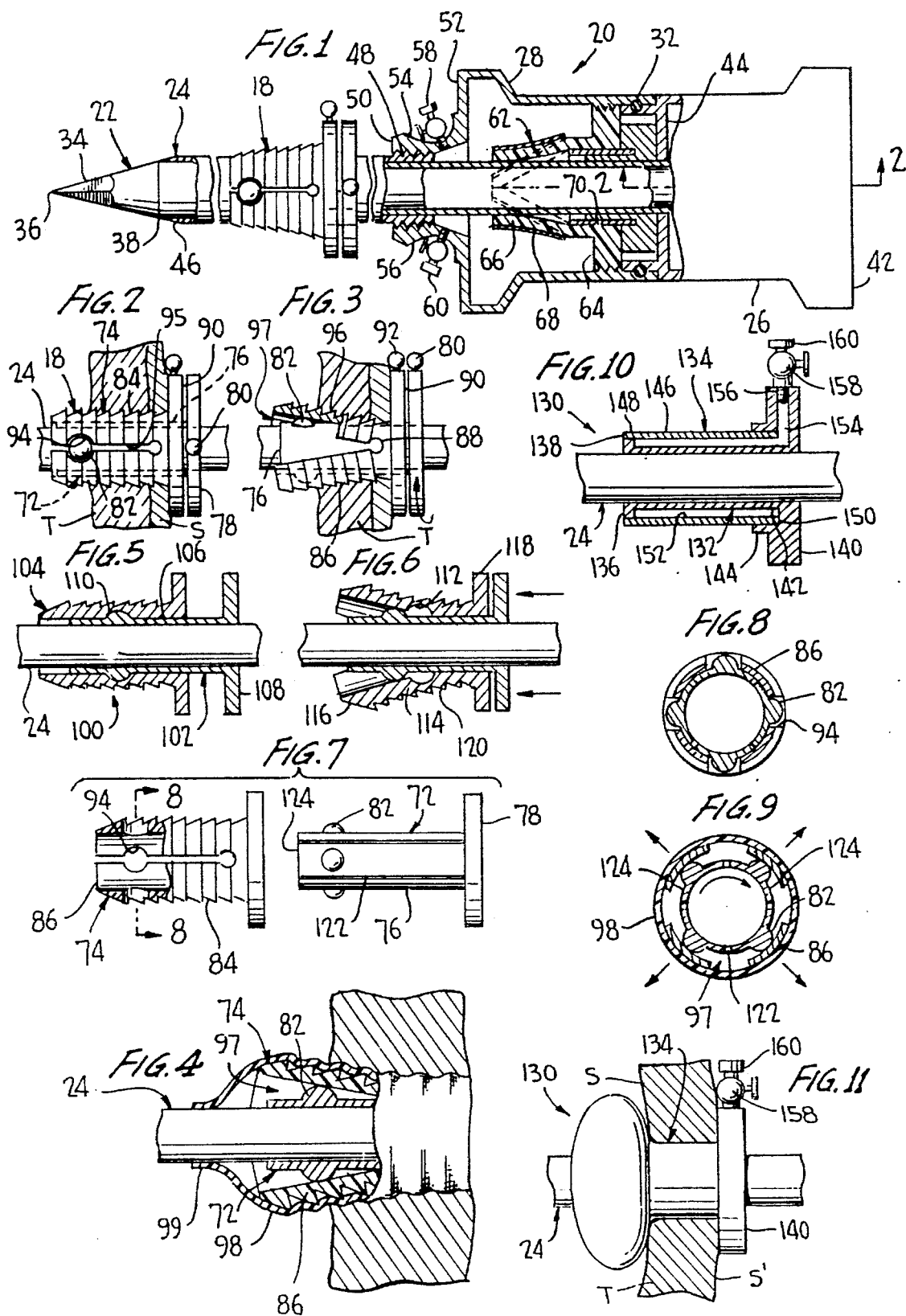

SURGICAL INSTRUMENT STABILIZER

This application is a divisional of prior application Ser. No. 08/170,620, filed Dec. 20, 1993, which is a continuation of prior application Ser. No. 07/788,143, filed Nov. 6, 1991, and now abandoned.

BACKGROUND OF THE INVENTION

1. Field of the Invention

The present invention pertains to surgical instruments for accessing cavities within the body and, more particularly, to surgical instruments for establishing communication with an anatomical cavity via insertion in a cavity wall.

2. Discussion of the Prior Art

Surgical penetrating instruments are widely used in surgical procedures to gain access to anatomical cavities ranging in size from the abdomen to small blood vessels, such as veins and arteries, epidural, plural and subachroniad spaces, heart ventricles and spinal and synovial cavities. Surgical penetrating instruments having a penetrating member and a portal sleeve have become extremely popular for use in establishing an endoscopic portal for many various procedures, most notably laproscopic procedures, with access to an anatomical cavity being established via the portal sleeve positioned to extend through a wall of the cavity upon penetration into the cavity by the penetrating member. Once the portal sleeve extends through the thickness of the cavity wall and projects into the cavity, it is desirable to stabilize or secure the portal sleeve in the cavity wall to prevent withdrawal or backing out of the portal sleeve from the cavity. With the portal sleeve secured relative to the cavity wall, insufflation of the cavity via the portal sleeve can be accomplished with greater safety, deflation of the cavity due to backing out of the portal sleeve can be prevented and, when several portal sleeves are utilized, instruments can be inserted via the portal sleeves without colliding in the cavity. In addition to portal sleeves, essentially solid members, such as uterine manipulators, are inserted in anatomical cavities via an opening therein for many surgical procedures; and, frequently, it is desirable to stabilize or lock the members in position to remain in the cavity during the surgical procedures without backing out therefrom.

Stabilizing devices including inflatable balloons or membranes for contacting, in an expanded state, an internal surface of tissue of a cavity wall and having bearing discs for contacting an external surface of the tissue have been proposed to secure surgical instruments relative to the cavity wall, and U.S. Pat. Nos. 5,002,557 to Hasson, 4,077,412 to Moosun, 3,459,175 to Miller and 3,253,594 to Matthews et al are illustrative of such devices. Additionally, portal sleeves having a spiral thread for engaging tissue of a cavity wall to prevent the portal sleeves from slipping out of the cavity after penetration by a trocar have been proposed, and exemplary portal sleeves are disclosed in U.S. Pat. No. 5,009,643 to Reich et al and sold by Storz Surgical Instruments as the Havlicek Trocar and Spiral Cannula.

Prior art stabilizers possess many disadvantages including difficulty in deploying the stabilizers during use, requiring a large contact area with the internal and external surfaces of tissue of a cavity wall, being immovably mounted on instruments to be stabilized such that the instruments must be secured in tissue at a fixed position along the instruments, increased trauma to tissue of the cavity wall, inability to reposition the portal sleeves once the stabilizers have been deployed, jamming and trapping of tissue in the stabilizers and, when inflatable balloons and membranes are utilized, susceptibility to failure due to accidental puncture prior to and during use.

SUMMARY OF THE INVENTION

Accordingly, it is a primary object of the present invention to overcome the aforementioned disadvantages of prior art stabilizers for surgical instruments positioned to extend through a wall of an anatomical cavity.

Another object of the present invention is to provide a stabilizer movable between contracted and expanded positions and having ribs facilitating insertion of the stabilizer in the contracted position in a wall of an anatomical cavity and resisting backing out of the stabilizer from the cavity wall in the expanded position.

A further object of the present invention is to provide a stabilizer movable between contracted and expanded positions with or without requiring inflation of the stabilizer.

It is also an object of the present invention to provide a stabilizer having an expandable outer member and a relatively movable, inner member for mechanically moving the outer member between contracted and expanded positions.

An additional object of the present invention is to provide a stabilizer movable along a surgical instrument such that the stabilizer can be inserted in tissue forming an anatomical cavity wall after selective positioning of the instrument to extend through the cavity wall and project into the cavity from the wall a desired depth.

The present invention has an additional object in that the stabilizer is movable along a surgical instrument to be stabilized such that movement of the stabilizer allows the instrument to be secured in tissue of a cavity wall at selective positions along the instrument.

Yet another object of the present invention is to provide a stabilizer having tapered annular ribs for engaging tissue along the thickness of a cavity wall.

A still further object of the present invention is to provide a stabilizer insertable in a cavity wall and having an expandable membrane for preventing trapping and jamming of tissue in the stabilizer.

The present invention has a further object in that the stabilizer can be used universally to secure both cannulated and solid surgical instruments in a position extending through an opening in an anatomical cavity and prevent backing out of the instruments from the cavity.

Some of the advantages of the present invention are that the stabilizer can be inserted in a cavity wall with minimal trauma to tissue and does not require a large contact area with tissue along the interior surface of a cavity wall, tissue is gripped along the thickness of the cavity wall, instruments can be stabilized in a cavity wall at various positions along the lengths of the instruments, instruments being stabilized do not have to be hollow or cannulated and the stabilizer can be constructed to be reusable or disposable for single patient use.

Accordingly, the stabilizer of the present invention is characterized in a tubular inner member concentrically, slidably disposed on a surgical instrument, such as a portal sleeve or uterine manipulator, to be stabilized and an expandable, outer member receiving the inner member to permit movement of the inner member relative to the outer member for moving the outer member between contracted and expanded positions. The outer member includes an expandable body formed of legs having recesses therein to receive protrusions on the inner member when the stabilizer is in the contracted position such that the legs extend longitudinally along the surgical instrument. A plurality of tapered ribs are carried on an outer surface of the legs to facilitate insertion of the stabilizer in the contracted position in a cavity wall and to resist backing out from the cavity wall when the stabilizer is moved to the expanded position. With the surgical instrument positioned to pass through a cavity wall such that a portion of the instrument projects into the anatomical cavity a desired depth, the stabilizer in the contracted position is moved along the surgical instrument and into the tissue forming the cavity wall. The inner member is then moved relative to the outer member causing the protrusions to engage inner surfaces of the legs and cam the legs outwardly from the surgical instrument to the expanded position. With the stabilizer in the expanded position, the legs are forced in biting engagement with tissue along the thickness of the cavity wall and apply force to the protrusions causing the inner member to tightly engage the surgical instrument. An expandable membrane can be disposed over the outer member in the contracted position such that spaces between the legs formed when the outer member expands are covered by the membrane to prevent jamming and trapping of tissue in the stabilizer. The outer member can include a balloon inflatable to assume the contracted and expanded positions.

The present invention is further characterized in a method of establishing an endoscopic portal in a wall of an anatomical cavity comprising the steps of positioning a portal sleeve to extend through the cavity wall into the cavity, moving a stabilizer in a contracted position distally along the portal sleeve into the cavity wall, and expanding the stabilizer to an expanded position to engage the cavity wall and hold the portal sleeve in the cavity wall.

Other objects and advantages of the present invention will become apparent from the following description of the preferred embodiments taken in conjunction with the accompanying drawings.

BRIEF DESCRIPTION OF THE DRAWINGS

FIG. 1 is a broken side view, partly in section, of a surgical instrument stabilizer according to the present invention in combination with a surgical penetrating instrument.

FIG. 2 is a broken side view, partly in section, of another embodiment of the surgical instrument stabilizer in a contracted position.

FIG. 3 is a broken side view, partly in section, of the surgical instrument stabilizer of FIG. 2 in an expanded position.

FIG. 4 is a broken side view, partly in section, of the surgical instrument stabilizer of FIG. 3 with an expandable membrane over the stabilizer.

FIG. 5 is a broken side view, partly in section, of another embodiment of the surgical instrument stabilizer in a contracted position.

FIG. 6 is a broken side view, partly in section, of the surgical instrument stabilizer of FIG. 5 in an expanded position.

FIG. 7 is an exploded view, partly in section, of another embodiment of the surgical instrument stabilizer.

FIG. 8 is a cross-sectional view taken along line 8—8 of FIG. 7.

FIG. 9 is a cross-sectional view taken along line 8—8 of FIG. 7 with the surgical instrument stabilizer in the expanded position and the expandable membrane disposed over the stabilizer.

FIG. 10 is a broken side view, partly in section, of another embodiment of the surgical instrument stabilizer in a contracted position.

FIG. 11 is a broken side view of the surgical instrument stabilizer of FIG. 10 in an expanded position in tissue of a cavity wall.

DESCRIPTION OF THE PREFERRED EMBODIMENTS

A stabilizer 18 according to the present invention is illustrated in FIG. 1 for use with a penetrating instrument 20 including an elongate penetrating member 22, an elongate portal sleeve 24 concentrically disposed around penetrating member 22, a hub 26 mounting penetrating member 22 and a housing 28 mounting portal sleeve 24, with the stabilizer 18 being disposed on portal sleeve 24. The hub 26 and the housing 28 can be unconnected, or the hub 26 can be latched to housing 28 with the use of any suitable releasable mechanism, such as ball detents 32, allowing the hub to be removed from the housing withdrawing the penetrating member from the portal sleeve. Accordingly, the penetrating instrument can be considered to be formed of a portal unit and a penetrating member unit, the portal unit including portal sleeve 24, and housing 28 and the penetrating member unit including penetrating member 22 and hub 26.

Penetrating member 22 is preferably made from a cylindrical or solid length of a rigid or flexible, medically acceptable, material such as stainless steel or plastic, with a diameter dependent upon the surgical procedure to be performed and the anatomical cavity to be penetrated. The penetrating member has a distal end 34 terminating at a sharp tip 36 for penetrating anatomical tissue; and, as shown in FIG. 1, the distal end 34 of the penetrating member is configured as a trocar having a solid, pyramidal shape with three, equally spaced facets forming tip 36 and terminating proximally at a cylindrical body 38 which, in turn, terminates proximally at a proximal end 40 secured to an end wall 42 of hub 26 by any suitable means, such as cement or threads. It will be appreciated that penetrating member 22 is shown as a trocar by way of example only, that the distal end of the penetrating member can have any desired configuration dependent on the surgical procedure to be performed and that the penetrating member can be solid or hollow or cannulated.

Hub 26 is preferably made of plastic to reduce cost and has an external configuration to cooperate with housing 28 to be easily grasped with one hand for use in penetrating tissue. Hub 26 is substantially rectangular in cross-section and includes, as best shown in FIG. 1, four side walls extending from a front wall 44 to end wall 42 to provide a rearwardly flared outer profile.

Portal sleeve 24 is preferably made of a cylindrical length of stainless steel or other suitable, medically acceptable, plastic or metal material and can be rigid or flexible and transparent or opaque. The portal sleeve has a distal end 46 and a threaded proximal end 48 received in an internally threaded nipple 50 extending from a front wall 52 of housing 28. Housing 28 is preferably made of plastic to reduce cost and has a rectangular configuration in cross-section corresponding to the cross-sectional configuration of hub 26 with a flared external profile adjacent front wall 52 to facilitate grasping during use. Recesses 54 and 56 are formed on opposite sides of nipple 50 and have a size and configuration to receive ball-type stop cocks 58 and 60, respectively, in a position such that the stop cocks are protected from inadvertent contact which could cause breakage or malfunction. A valve assembly 62 is mounted in housing 28 to control flow through the portal sleeve once the penetrating member unit is removed therefrom. The valve assembly can have any acceptable configuration and, as shown, includes a flange 64 having an annular configuration with a threaded periphery to be threadedly secured in housing 28, a plurality of spaced, spreadable legs 66 extending distally from flange 64 to produce a normally conical configuration tapering to an apex as illustrated in dashed lines in FIG. 1, and a conical stretchable sleeve 68, preferably made of a rubber-like material such as silicone, having a configuration to tightly fit over legs 66 such that the sleeve and legs are normally biased to the closed position at the apex to prevent passage of fluids through the valve assembly. The legs 66 and flange 64 are preferably integrally made of unitary construction of a material, such as a plastic, nylon, facilitating movement of medical instruments therethrough and allowing legs 66 to flex. The legs 66 are concentrically disposed around a central opening 70 in flange 64 and are slightly spaced from each other by gaps which terminate at curved relief recesses.

The stabilizer 18 includes a stabilizer body longitudinally, slidably disposed on the portal sleeve and formed of an inner member 72 and an outer member 74 relatively movable with respect to each other to have a contracted position, as shown in FIGS. 1 and 2, and an expanded position, as shown in FIG. 3. The inner member 72 includes a tube 76 movably, concentrically disposed on portal sleeve 24 and having a diameter to allow frictional engagement with the portal sleeve and an annular flange 78 extending transversely from a rear or proximal end of the tube 76 and carrying a knob 80 acting as an index marker and a structure for grasping by the surgeon to operate the stabilizer. At a forward or distal end, tube 76 carries a plurality of knob-like protrusions 82 preferably having smoothly curving configurations such as hemispheric. The outer member 74 includes an expandable portion 84 formed of a plurality of legs 86 arranged around a longitudinal axis of the portal sleeve and interconnected at radiused ends 88, the legs extending from a transverse flange 90 carrying a knob 92 cooperating with knob 80 to operate as an indicator and to be grasped by the surgeon. Recesses 94 are formed in lateral edges of the legs at positions to receive protrusions 82 when the stabilizer is in the contracted position, and the lateral edges of the legs extend along the portal sleeve parallel with the longitudinal axis of the portal sleeve in the contracted position. Spaces 95 are disposed between the legs 86 with a width defined between the lateral edges as shown in FIG. 2. The outer surface of body 84 carries a plurality of annular ribs 96 tapering distally to facilitate insertion of the stabilizer in tissue and resist movement of the stabilizer out of the tissue. In the embodiment of FIGS. 2 and 3, the annular ribs 96 have equal major diameters to produce a generally cylindrical configuration along the body 84, while the major diameters of the ribs gradually increase in a proximal direction in the embodiment shown in FIG. 1 to produce a generally conical configuration. From the discussion of the operation of the stabilizer, it will be appreciated that the outer configuration of expandable portion 84 will vary dependent upon the tissue or cavity wall penetrated with the surgical penetrating instrument and that the outer surface can have smooth as well as irregular or ribbed configurations. The inner and outer members can be made of any medically acceptable material; however, plastic is preferred to permit inexpensive, unitary, integral one-piece manufacture and allow the stabilizer to be disposable after single patient use.

In use, after penetration of the penetrating member 22 into a cavity and selective positioning of the portal sleeve 24 to extend through a wall of the cavity a desired depth into the cavity, the stabilizer 18 is moved distally along the portal sleeve such that the stabilizer is inserted in tissue T forming the cavity wall with flange 90 abutting an external surface of the tissue, as shown in FIG. 2, such as skin S. The inner and outer members 72 and 74 are in the contracted position during insertion with protrusions 82 received in recesses 94 to reduce tissue resistance; and, once the stabilizer is fully inserted, inner member 72 is rotated 90° relative to outer member 74 to align knobs 80 and 92, as shown in FIG. 3, causing protrusions 82 to move out of recesses 94 and engage the inner surfaces of legs 86 to cam the legs angularly outwardly from the longitudinal axis of the portal sleeve to the expanded position. With the body in the expanded position, the lateral edges of the legs will be angularly disposed relative to the portal sleeve longitudinal axis and the width of spaces 95 will increase in size. Accordingly, a concentric space 97 is formed between the inner and outer members in the expanded position, and the concentric space 97 increases in size diametrically in a distal direction. In other words, the outer diameter of the stabilizer along the legs is greater at a distal end of the legs than a proximal end of the legs in the expanded position to prevent withdrawal of the stabilizer and, therefore, the portal sleeve, from tissue of the cavity wall. At the same time, the opposite force applied by the legs 86 to the protrusions 82 causes the tube 76 to engage the portal sleeve 24 with greater force to further stabilize the portal sleeve in the tissue. Where ribs 96 are provided, the legs 86 will be forced into biting engagement with surrounding tissue along the thickness of the cavity wall to lock the stabilizer in place in the tissue. With the penetrating member unit withdrawn from the portal unit, instruments can be inserted and gas for insufflation can be introduced at the cavity via the portal sleeve dependent upon the surgical procedure being performed while the portal sleeve is held in a stable position not subject to inadvertent movement or withdrawal. Once the surgical procedure has been completed, the inner member is again rotated 90° relative to the outer member to align protrusions 82 with recesses 94 to return the stabilizer to the contracted position facilitating withdrawal of the stabilizer and the portal sleeve from the cavity wall.

A cylindrical, flexible, expandable or stretchable sleeve or membrane 98 for use with the stabilizer 18 is shown in FIG. 4. Membrane 98 is preferably made of a rubber-like material, such as silicone, having a configuration to fit closely over outer member 74 such that the spaces formed between the lateral edges of the legs 86 when the legs are spread apart in the expanded position are covered, thusly preventing trapping or jamming of tissue in the stabilizer. In some instances, it may be desirable to form membrane 98 to extend over a portion of the portal sleeve 24 disposed within the cavity such that a neck 99 of the membrane 98 covers the concentric space 97 formed between the outer member 74 and the inner member 72 in the expanded position to prevent tissue from becoming caught between the outer and inner members. Membrane 98 can be made to deform around the configuration of the outer member 74, or the membrane 98 can be formed with a predetermined configuration, such as a ribbed configuration, corresponding to the configuration of the outer member 74.

A modification of the stabilizer 18 is illustrated in FIGS. 5 and 6 at 100, stabilizer 100 differing from stabilizer 18 primarily in that the stabilizer 100 is operated by relative longitudinal movement of an inner member 102 relative to an outer member 104 of the stabilizer body rather than the rotational movement required of the stabilizer 18. The inner member 102 includes a tube 106 having a diameter to frictionally engage portal sleeve 24 and an annular flange 108 extending transversely from a rear or proximal end of tube 106. Protrusions 110 are carried on a distal end of the tube 106 at positions to engage recesses 112 in legs 114 forming an expandable portion 116 on the outer member 104 terminating proximally at a transverse flange 118.

In the contracted position with protrusions 110 engaged with recesses 112, the flange 108 is spaced proximally from the flange 118 as shown in FIG. 5. In use, after the portal sleeve 24 is selectively positioned in the tissue, the stabilizer 100 is inserted in tissue in the contracted position shown in FIG. 5 by moving the stabilizer along the portal sleeve in the same manner described above. The inner member 102 is moved longitudinally distally relative to the outer member 104 to force protrusions 110 distally camming the legs 114 outwardly from the longitudinal axis of the portal sleeve to the expanded position illustrated in FIG. 6 such that the outer diameter of the stabilizer at a distal end of the legs is greater than the outer diameter at a proximal end of the legs to prevent withdrawal of the stabilizer from the tissue. The tapered ribs 120 on an outer surface of the legs 114 bite into the tissue to hold the stabilizer relative to the tissue, and the force applied by the legs 114 to the protrusions 110 cause the tube 106 to grip the portal sleeve to further stabilize the position thereof.

Another modification of stabilizer 18 is illustrated in FIGS. 7–9 wherein the stabilizer is substantially the same as that shown in FIGS. 2 and 3 with the exception that the expandable portion 84 is formed of four equally spaced legs 86 and four equally spaced protrusions 82 are disposed around the tube 76 of the inner member 72. Additionally, longitudinal slots 122 are formed in the tube 76 centrally between protrusions 82 and extend from a distal end of the tube 76 to the flange 78 to form fingers 124. Use of the stabilizer of FIG. 7 is similar to that described above with FIG. 8 illustrating the stabilizer in the contracted position with the protrusions 82 received in the recesses 94 of the expandable portion 84. The expanded position is illustrated in FIG. 9 wherein the inner member 72 has been rotated 45° such that the protrusions 82 engage the inner surfaces of legs 86 to expand each of the four legs outwardly from the portal sleeve longitudinal axis thereby increasing the outer diameter of the stabilizer at a distal end of the legs relative to the outer diameter at a proximal end of the legs and causing the ribs to bite into the tissue of the cavity wall. The opposite force applied by the legs 86 to the protrusions 82 causes fingers 124 to tightly grip the portal sleeve for further stabilization.

As shown in FIG. 9, membrane 98 can be disposed over the outer member 74 such that the spaces formed between lateral edges of the legs 86 in the expanded position are covered to prevent tissue from being caught therein.

Another modification of the stabilizer 18 is illustrated in FIGS. 10 and 11 at 130 and includes a stabilizer body formed of an inner tubular member 132 movably disposed on portal sleeve 24 and an outer tubular member 134 receiving the inner member 132. Inner member 132 has a radial shoulder 136 on a distal end 138 thereof and a transverse flange 140 on a proximal end 142 thereof, the proximal end of the inner member 132 being concentrically received in a tubular neck 144 projecting distally from the flange 140. Outer member 134 includes an expandable flexible and resilient balloon or membrane 146 preferably made of a rubber-like material, such as silicone, and having a distal end 148 secured on shoulder 136 and a proximal end 150 received in neck 144. The proximal end 150 of the outer member is secured to an inner surface of the neck 144 such that an annular chamber 152 is defined between the inner and outer members to extend between the shoulder 136 and the flange 140. A passage 154 is formed in the flange 140 with an opening 156 on an external surface of the flange communicating with the chamber 152. A valve 158, such as a stop-cock, is disposed in opening 156 to selectively seal chamber 152 and prevent the ingress and egress of fluids therethrough in a closed position for the valve. Valve 158 includes a coupling 160 connectible with a source of fluid for selectively admitting fluid into chamber 152 via passage 154 in an open position for the valve.

In use, as shown in FIG. 11, portal sleeve 24 is positioned to extend through tissue T forming a wall of an anatomical cavity such that the portal sleeve projects into the cavity a desired depth from an internal surface S of the cavity wall. The stabilizer 130 is moved along the portal sleeve and inserted in the tissue until the flange 140 abuts an external surface, such as skin S', of the cavity wall. The outer member 134 is in a contracted, or unexpanded, position during insertion facilitating advancement of the stabilizer 130 in the tissue. With the flange 140 abutting external surface S', a substantial portion of the length of outer member 134 is disposed in the cavity from internal surface S. Coupling 160 is connected with a source of fluid, and valve 158 is opened admitting the fluid into passage 154 and, therefore, chamber 152 causing the portion of outer member 134 disposed in the cavity to expand outwardly from a longitudinal axis of the stabilizer while the portion of the outer member that is disposed along the thickness of the tissue, i.e., between surfaces S and S', remains unexpanded due to resistance from tissue T. Accordingly, the tissue is secured between the expanded portion of outer member 134 adjacent internal surface S and the flange 140 adjacent external surface S' such that movement of the stabilizer out of and further into the cavity is prevented. Additionally, pressure from the fluid in chamber 152 is exerted against the inner member 132 causing the inner member to tightly grip the portal sleeve for further stabilization thereof. Once the outer member has been expanded, valve 158 is closed to prevent escape of fluid from the chamber 152 and thusly maintain the expanded position for the stabilizer. With the penetrating member withdrawn from the portal sleeve 24, instruments can be inserted and gas for insufflation can be introduced at the cavity via the portal sleeve dependent upon the surgical procedure being performed while the portal sleeve is held in a stable position not subject to inadvertent movement or withdrawal. Once the surgical procedure has been completed, valve 158 is opened allowing fluid to escape from chamber 152 via opening 156 returning the outer member 134 to the contracted position facilitating withdrawal of the stabilizer from the cavity wall.

Having described preferred and alternative embodiments of a new and improved surgical instrument stabilizer, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In combination, a portal sleeve and a stabilizer for stabilizing the portal sleeve comprising a portal sleeve for being positioned to extend through an opening in an anatomical cavity wall and having a distal end for being positioned in the anatomical cavity, a proximal end for being positioned externally of the anatomical cavity and a longitudinal axis; and a stabilizer including a body disposed on said portal sleeve for being moved relative to said portal sleeve longitudinally, distally along said portal sleeve and into the opening, an expandable portion carried by said body for movement with said body along said portal sleeve and into the opening with said expandable portion in a contracted position wherein said expandable portion is disposed close to said portal sleeve to facilitate insertion of said body in and withdrawal of said body from the opening, said expandable portion being movable, while positioned in the opening, from said contracted position to an expanded position wherein said expandable portion is disposed further away from said portal sleeve to engage the cavity wall, means carried by said body for moving said expandable portion between said contracted and expanded positions and rib means disposed on said expandable portion for facilitating insertion of said body in the opening in said contracted position and resisting withdrawal of said body from the opening.

2. The combination recited in claim 1 wherein said rib means taper in the direction of insertion of said body in the opening.

3. The combination recited in claim 2 wherein said rib means include a plurality of annular ribs.

4. The combination recited in claim 3 wherein said ribs have a major diameter and said major diameters of said ribs are substantially the same to define a cylindrical configuration along said expandable portion in said contracted position.

5. The combination recited in claim 3 wherein said ribs have a major diameter and said major diameters of said ribs gradually decrease in size in the direction of insertion of said body to define a conical configuration along said expandable portion in said contracted position.

6. In combination, a portal sleeve and a stabilizer for stabilizing the portal sleeve comprising a portal sleeve for being positioned to extend through an opening in an anatomical cavity wall and having a distal end for being positioned in the anatomical cavity and a proximal end for being positioned externally of the anatomical cavity; and a stabilizer including a plurality of legs slidably disposed on said portal sleeve, said legs extending distally along said portal sleeve to terminate at free ends, said legs being movable from a normally contracted position wherein said free ends are disposed close to said portal sleeve to an expanded position wherein said free ends are disposed further away from said portal sleeve, said legs being movable relative to said portal sleeve longitudinally, distally along said portal sleeve and into the opening with said legs in said contracted position, and means for moving said legs from said contracted position to said expanded position once said legs have been moved into the opening to cause said legs to engage the anatomical cavity wall.

7. The combination recited in claim 6 wherein said stabilizer further includes an expandable membrane surrounding said leg.

8. In combination, a portal sleeve and a stabilizer for stabilizing the portal sleeve comprising a portal sleeve for being positioned to extend through an opening in an anatomical cavity wall and having a distal end for being positioned in the anatomical cavity, a proximal end for being positioned externally of the anatomical cavity and a longitudinal axis; and a stabilizer including a body disposed on said portal sleeve for being moved relative to said portal sleeve longitudinally, distally along said portal sleeve and into the opening, an expandable portion carried by said body for movement with said body along said portal sleeve and into the opening with said expandable portion in a contracted position wherein said expandable portion is disposed close to said portal sleeve to facilitate insertion of said body in and withdrawal of said body from the opening, said expandable portion including a plurality of legs extending along said longitudinal axis in said contracted position and extending outwardly of said longitudinal axis in an expanded position, said expandable portion being movable, while positioned in the opening, from said contracted position to said expanded position to engage the cavity wall and means carried by said body for moving said expandable portion between said contracted and expanded positions, said body including an inner member slidably disposed on said portal sleeve, said expandable portion including an outer member disposed over said inner member and carrying said legs, said inner member being relatively, movably disposed in said outer member and said means for moving including protrusions on said inner member for camming said legs outwardly in response to movement of said inner member relative to said outer member.

9. The combination recited in claim 8 wherein said legs have recesses for receiving said protrusions in said contracted position.

10. The combination recited in claim 9 wherein said legs include inner surfaces for applying force to said protrusions in said expanded position to cause said inner member to engage said portal sleeve.

11. The combination recited in claim 10 wherein said legs include lateral edges extending longitudinally along said portal sleeve parallel with said longitudinal axis in said contracted position and said recesses are formed in said lateral edges.

12. The combination recited in claim 11 wherein said protrusions have a smoothly curving configuration.

13. The combination recited in claim 10 wherein said inner member includes a tube for receiving said portal sleeve and further including slots in said tube disposed between said protrusions and extending longitudinally along said tube to form fingers for gripping said portal sleeve when said inner surfaces apply force to said protrusions.

14. The combination recited in claim 8 wherein said inner member has a proximal end and further including a flange on said inner member proximal end and a knob on said inner member flange for rotating said inner member relative to said outer member to move said expandable portion between said contracted and expanded positions.

15. The combination recited in claim 14 wherein said outer member has a proximal end and further including a flange on said outer member proximal end and a knob on said outer member flange for being aligned with said knob on said inner member flange in said expanded position.

16. The combination recited in claim 8 wherein said outer member has a proximal end carrying a flange and said inner member has a proximal end carrying a flange, said inner member flange being spaced longitudinally from said outer member flange in said contracted position and being movable longitudinally toward said outer member flange to abut said outer member flange in said expanded position.

17. The combination recited in claim 8 and further comprising a stretchable membrane disposed around said legs for preventing tissue forming the anatomical cavity wall from being trapped between said legs.

18. The combination recited in claim 17 wherein said membrane includes a neck disposed in engagement with a portion of said portal sleeve disposed within the anatomical cavity.

19. The combination recited in claim 17 wherein spaces are defined between said legs in said expanded position, and wherein said membrane is disposed over said spaces.

20. In combination, a portal sleeve and a stabilizer for stabilizing the portal sleeve comprising a portal sleeve for being positioned to extend through an anatomical cavity wall and having a distal end for being disposed in the anatomical cavity and a proximal end for being disposed externally of the anatomical cavity; and a stabilizer including a body comprising a first tubular member slidably disposed on said portal sleeve for longitudinal movement therealong to be inserted in the cavity wall between the cavity wall and said portal sleeve, said body including a distal portion for positioning adjacent an internal surface of the cavity wall, a proximal portion for positioning adjacent an external surface of the cavity wall, an expandable portion carried by said first tubular member to extend along said portal sleeve, said expandable portion being movable between a contracted position wherein said expandable portion is disposed close to said portal sleeve for facilitating insertion of said body in the cavity wall and an expanded position adjacent said distal portion of said body wherein said expandable portion is disposed further away from said portal sleeve for engaging the internal surface of the cavity wall to resist withdrawal of said body and said portal sleeve from the cavity wall, said expandable portion including a plurality of legs disposed around said portal sleeve, said legs having distal ends disposed close to said portal sleeve in said contracted position and disposed further away from said portal sleeve in said expanded position, said body being movable relative to and along said portal sleeve to be inserted in the cavity wall with said expandable portion in said contracted position, and means for moving said expandable portion between said contracted and expanded positions.

21. The combination recited in claim 20 and further including a second tubular member receiving said first tubular member and movable with said first tubular member along said portal sleeve, said legs being disposed on said second tubular member, said first tubular member being movable relative to said second tubular member.

22. The combination recited in claim 21 wherein said second tubular member includes an inner wall surface and said means for moving includes means on said first tubular member for selectively engaging and disengaging said inner wall surface in response to movement of said first tubular member relative to said second tubular member.

23. The combination recited in claim 22 wherein said first tubular member is rotatable relative to said second tubular member.

24. The combination recited in claim 22 wherein said first tubular member is movable longitudinally relative to said second tubular member.

25. The combination recited in claim 22 wherein said expandable portion includes an expandable membrane disposed around said legs.

26. In combination, a portal sleeve and a stabilizer for stabilizing the portal sleeve comprising a portal sleeve for being positioned to extend through an anatomical cavity wall and having a distal end for being disposed in the anatomical cavity and a proximal end for being disposed externally of the anatomical cavity; and a stabilizer including a plurality of legs slidably disposed on said portal sleeve, said legs extending longitudinally, distally along said portal sleeve to terminate at distal ends, said legs being movable between a contracted position wherein said distal ends of said legs are disposed close to said portal sleeve and an expanded position wherein said distal ends of said legs are disposed further away from said portal sleeve, said legs being movable relative to and along said portal sleeve to be inserted in the cavity wall with said legs in said contracted position, and means disposed between said portal sleeve and said legs for moving said legs from said contracted position to said expanded position.

27. The combination recited in claim 26 wherein said legs have a length in said expanded position to engage the tissue forming the cavity wall along the thickness of the cavity wall.

28. A method of establishing an endoscopic portal in a wall of an anatomical cavity comprising the steps of providing a portal sleeve and a stabilizer including a plurality of legs slidably disposed on the portal sleeve, the legs extending distally along the portal sleeve to terminate at distal ends, the legs being movable from a contracted position wherein the distal ends of the legs are disposed close to the portal sleeve to an expanded position wherein the distal ends of the legs are disposed further away from the portal sleeve;

positioning the portal sleeve to extend through the cavity wall into the cavity;

advancing the legs distally along the portal sleeve into the cavity wall with the legs in the contracted position; and moving the legs from the contracted position to the expanded position to cause the legs to engage the cavity wall and hold the portal sleeve in the cavity wall.

29. A method as recited in claim 28 wherein said advancing step includes moving the legs to a position where the distal ends of the legs are disposed within the cavity.

* * * * *